(12) United States Patent
Chungi et al.

(10) Patent No.: US 6,306,436 B1
(45) Date of Patent: Oct. 23, 2001

(54) STABILIZED, ACID-FREE FORMULATION FOR SUSTAINED RELEASE OF BUPROPION HYDROCHLORIDE

(75) Inventors: Shubha Chungi; Kangwen Lin, both of Sharon, MA (US)

(73) Assignee: Teva Pharmaceuticals USA, Inc., North Wales, PA (US)

( * ) Notice: Subject to any disclaimer, the term of this patent is extended or adjusted under 35 U.S.C. 154(b) by 0 days.

(21) Appl. No.: 09/562,240

(22) Filed: Apr. 28, 2000

(51) Int. Cl.$^7$ ............... A61K 9/20; A61K 9/22; A61K 9/28; A61K 9/14; A61K 47/00
(52) U.S. Cl. ............ 424/464; 424/468; 424/465; 424/474; 424/488; 514/772.3; 514/781
(58) Field of Search ................ 424/464, 473, 424/465, 468, 474, 469, 488; 514/772.3, 781

(56) References Cited

U.S. PATENT DOCUMENTS

| | | |
|---|---|---|
| 3,819,706 | 6/1974 | Mehta . |
| 3,885,046 | 5/1975 | Mehta . |
| 5,358,970 | 10/1994 | Ruff et al. . |
| 5,427,798 | 6/1995 | Ludwig et al. . |
| 5,541,231 | 7/1996 | Ruff et al. . |
| 5,731,000 | 3/1998 | Ruff et al. . |
| 5,763,493 | 6/1998 | Ruff et al. . |
| 5,968,553 | 10/1999 | Maitra et al. . |
| 6,120,803 | * 9/2000 | Wong et al. .......... 424/473 |

FOREIGN PATENT DOCUMENTS

| | | |
|---|---|---|
| WO 99/33456 | 7/1999 | (WO) . |
| WO 99/33457 | 7/1999 | (WO) . |

OTHER PUBLICATIONS

Physician Desk Reference, 54th edition, 2000, pp. 1329–1333.*

Laizure et al. (1985), "Stability of Bupropion and Its Major Metabolites in Human Plasma," *Therapeutic Drug Monitoring* 7(4):447–450.

Walters (1980), "Influence of pH on Hydrolytic Decomposition of Diethylpropion Hydrochloride: Stability Studies on Drug Substance and Tablets Using High–Performance Liquid Chromatography," *J. Pharm. Sci.* 69(10):1206–1209.

* cited by examiner

*Primary Examiner*—Thurman K. Page
*Assistant Examiner*—Blessing Fubara
(74) *Attorney, Agent, or Firm*—Dianne E. Reed; J. Elin Hartrum; Reed & Associates

(57) ABSTRACT

Stabilized bupropion hydrochloride pharmaceutical compositions are disclosed that are free of acid additives and provide for a sustained release of the bupropion hydrochloride. The particulate bupropion hydrochloride may be coated with a membrane coating and large-size particles may also be used. Methods for treating individuals using the stabilized bupropion hydrochloride pharmaceutical compositions are also provided.

36 Claims, No Drawings

STABILIZED, ACID-FREE FORMULATION FOR SUSTAINED RELEASE OF BUPROPION HYDROCHLORIDE

TECHNICAL FIELD

The present invention relates generally to sustained release bupropion hydrochloride compositions, and more specifically relates to such compositions in which the drug is stabilized without added acid. The invention additionally relates to methods for administering bupropion using the novel formulations. The invention finds utility in the fields of drug delivery, pharmacology and medicine.

BACKGROUND

Bupropion is an antidepressant agent that is chemically distinct from tricyclic, tetracyclic and other commercially available antidepressants, e.g., selective serotonin-reuptake inhibitors, or "SSRIs." Bupropion, described in U.S. Pat. Nos. 3,819,706 and 3,885,046, is currently available as the hydrochloride salt, i.e., as m-chloro-α-(t-butylamino) propiophenone (amfebutamone) hydrochloride,

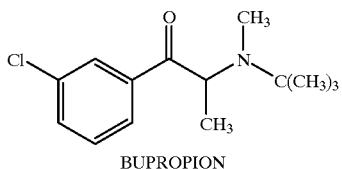

BUPROPION and is used as both an antidepressant and a smoking cessation aid. Utility in treating attention deficit hyperactivity disorder (ADHD) has also been evaluated. Bupropion hydrochloride is a water-soluble, crystalline solid having a melting point of 233–234° C., and is highly hygroscopic and susceptible to decomposition. Because of the drug's instability, the shelf-life of bupropion formulations has proved to be problematic, and those working in the field have tried a number of different approaches to improving the storage stability of the drug.

For example, U.S. Pat. Nos. 5,541,231, 5,763,493, 5,358,970, and 5,731,000 to Ruff et al. describe bupropion hydrochloride formulations that use an organic acid, a carboxylic acid, an amino acid salt (e.g., cysteine hydrochloride, glycine hydrochloride, and cysteine dihydrochloride), or sodium metabisulfite as a stabilizer. PCT Publication No. WO 99/33457 to Kulkani et al. describes bupropion hydrochloride formulations containing dicarboxylic acids as stabilizing agents. U.S. Pat. No. 5,968,553 to Maitra et al. describes bupropion hydrochloride formulations containing dilute inorganic acids as stabilizers including hydrochloric acid, phosphoric acid, nitric acid, and sulfuric acid. Acid stabilization of the related compound diethylpropion hydrochloride has also been described by Walters (1980) *J. Pharm. Sci.* 69(10):1206–1209. Placing bupropion HCl in a relatively low pH environment has proven effective in stabilizing bupropion and its major metabolites in human plasma; see Laizure et al. (1985) *Ther. Drug Monit.* 7(4):447–450. Unfortunately, the use of acidic materials in pharmaceutical formulations requires costly production procedures and equipment. Therefore, it would be desirable to produce a stabilized bupropion hydrochloride formulation without the use of acid stabilizers.

Pharmaceutical dosage forms are known which provide a variety of drug release profiles, including immediate release, delayed release, and sustained release. An immediate release formulation provides for drug release immediately following drug administration, while delayed release (also termed "site-specific release") formulations prevent drug release until a certain point in the body is reached, and "sustained release" formulations provide substantially continuous release over a predetermined time period (so-called "sustained release"). As the incidence of seizures is reduced by use of sustained release bupropion hydrochloride formulations, (See Physicians Desk Reference, 1999 Edition, page 1279), sustained release formulations are particularly preferred for administration of the drug. Sustained release formulations have been described, for example, in U.S. Pat. No. 5,427,798 to Ludwig et al. These formulations control drug release by varying the surface area to volume ratio of the tablet. Unfortunately, the Ludwig et al. formulations rely on the inclusion of acids to stabilize the bupropion hydrochloride.

The present invention is directed to a novel means for stabilizing bupropion hydrochloride in a sustained release formulation without having to incorporate an added acid in the formulation. Accordingly, the present invention provides novel bupropion hydrochloride formulations that are sustained release and have substantially improved storage stability but are acid-free. No art of which applicants are aware describes sustained release bupropion hydrochloride formulations as now provided herein.

To the best of applicants' knowledge, the pharmaceutical formulations of the invention are previously unknown and completely unsuggested by the art.

SUMMARY OF THE INVENTION

It is a primary object of the invention to provide a bupropion hydrochloride pharmaceutical composition for oral administration that is free of added acid, provides for sustained release of the active agent from the dosage form, and contains at least about 80 wt. % of undegraded bupropion hydrochloride after storage for three months at about 40° C. and 75% relative humidity.

It is another object of the invention to provide a bupropion hydrochloride pharmaceutical composition for oral administration in the form of a compressed tablet containing bupropion hydrochloride crystals coated with a cellulosic polymer that is free of added acid, provides for sustained release of the active agent from the dosage form, and contains at least about 90 wt. % of undegraded bupropion hydrochloride after storage for three months at about 40° C. and 75% relative humidity.

It is another object of the invention to provide a method for preparing a stabilized bupropion hydrochloride composition for oral administration without addition of acid by admixing bupropion hydrochloride with a pharmaceutically acceptable carrier and compressing the admixture into a tablet, wherein the bupropion hydrochloride has a particle size in the range of 75µ to 900µ.

It is a still further object of the invention to provide a method for preparing a bupropion hydrochloride pharmaceutical composition for oral administration without addition of acid by coating particulate bupropion hydrochloride with an amount of a cellulosic polymer, admixing the coated bupropion hydrochloride with a suitable amount of a pharmaceutically acceptable carrier and compressing the resulting admixture into a tablet.

In one aspect of the invention, then, a sustained release bupropion hydrochloride pharmaceutical composition is provided that is free of acid additives. The composition provides for sustained release of the bupropion hydrochloride from the dosage form and contains at least about 80 wt. % of undegraded bupropion hydrochloride after storage for three months at about 40° C. and 75% relative humidity. The bupropion hydrochloride may be in the form of crystals and may be coated with a cellulosic polymer.

In another aspect of the invention, a method for preparing the pharmaceutical composition is provided, comprising the steps of admixing particulate bupropion hydrochloride with a pharmaceutically acceptable carrier and compressing the admixture into a tablet. The bupropion hydrochloride may be in a crystalline form that is coated with a cellulosic polymer prior to admixture with the pharmaceutically acceptable carrier.

In another aspect of the invention, a method of treating a patient suffering from depression or nicotine addiction is provided. The method comprises orally administering to the patient the pharmaceutical composition of the present invention, within the context of a dosing regimen effective to treat the particular condition. When used to treat nicotine addiction, the pharmaceutical composition may be administered in combination with an effective amount of nicotine.

DETAILED DESCRIPTION OF THE INVENTION

DEFINITIONS AND NOMENCLATURE:

Before the present formulations and methods of use are disclosed and described, it is to be understood that unless otherwise indicated this invention is not limited to specific pharmaceutical carriers, other formulation components, or particular administration regimens, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a coating" includes multiple coatings, reference to "a pharmaceutical carrier" includes combinations of two or more carriers, and the like.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not.

The term "bupropion hydrochloride" as used herein refers to the hydrochloride salt of m-chloro-α-(t-butylamino)propiophenone.

By the terms "effective amount" or "therapeutically effective amount" of an agent as provided herein are meant a nontoxic but sufficient amount of the agent to provide the desired therapeutic effect. As will be pointed out below, the exact amount required will vary from subject to subject, depending on age, general condition of the subject, the severity of the condition being treated, and the particular active agent administered, and the like. Thus, it is not possible to specify an exact "effective amount." However, an appropriate "effective" amount in any individual case may be determined by one of ordinary skill in the art using routine experimentation.

By "pharmaceutically acceptable" carrier is meant a carrier comprised of a material that is not biologically or otherwise undesirable, i.e., the material may be administered to an individual along with the active agent without causing any undesirable biological effects or interacting in a deleterious manner with any of the other components of the pharmaceutical composition in which it is contained. The term "carrier" is used generically herein to refer to any components present in the pharmaceutical formulations other than the active agent or agents, and thus includes diluents, binders, lubricants, fillers, coloring agents, wetting or emulsifying agents, preservatives, and the like.

The term "controlled release" is intended to refer to any drug-containing formulation in which release of the drug is not immediate, i.e., with a "controlled release" formulation, oral administration does not result in immediate release of the drug into an absorption pool. The term is used interchangeably with "nonimmediate release" as defined in Remington: *The Science and Practice of Pharmacy, Nineteenth Ed.* (Easton, Pa.: Mack Publishing Company, 1995). As discussed therein, immediate and nonimmediate release can be defined kinetically by reference to the following equation:

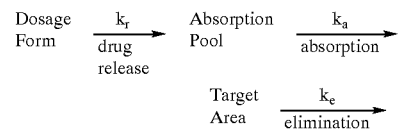

The absorption pool represents a solution of the drug administered at a particular absorption site, and $k_r$, $k_a$, and $k_e$ are first-order rate constants for (1) release of the drug from the formulation, (2) absorption, and (3) elimination, respectively. For immediate release dosage forms, the rate constant for drug release $k_r$, is far greater than the absorption rate constant $k_a$. For the controlled release formulations, that is, for the formulations of the present invention, the opposite is true, i.e., $k_r << k_a$, such that the rate of release of drug from the dosage form is the rate-limiting step in the delivery of the drug to the target area. The term "controlled release" includes any nonimmediate release formulation, including but not limited to sustained release, delayed release and pulsatile release formulations.

The term "sustained release" is used in its conventional sense to refer to a drug formulation that provides for gradual release of a drug over an extended period of time, and that preferably, although not necessarily, results in substantially constant blood levels of a drug over an extended time period.

"Enteric coating" or "enterically coated" as used herein relates to the presence of polymeric materials in a drug formulation that results in an increase in the drug's resistance to disintegration in the stomach. Typically, the polymeric material is present as a coating surrounding a drug-containing core, but the polymeric material may also be present in an admixture with the drug itself within a coated formulation.

STABILIZED BUPROPION HYDROCLORIDE FORMULATIONS:

The invention provides a pharmaceutical composition for oral administration comprised of a therapeutically effective amount of particulate, crystalline bupropion HCl and a pharmaceutically acceptable carrier that is free of added acid, provides for sustained release of the active agent from the dosage form and contains at least about 80 wt. % of undegraded bupropion hydrochloride after storage for three months at about 40° C. and 75% relative humidity. The particulate bupropion HCl may or may not be coated with a membrane coating material. In the preferred embodiment, the pharmaceutical composition is in the form of a compressed tablet and the particulate bupropion HCl is coated with a membrane coating material prior to tablet formulation. The pharmaceutical composition also contains a pharmaceutically acceptable carrier that provides for sustained release of the active agent.

The bupropion hydrochloride particles may be coated with a selected membrane coating material, typically although not necessarily a polymeric material or a combination of polymeric materials that is bioerodible, gradually hydrolyzable and/or gradually water-soluble. Suitable membrane coating materials include, but are not limited to: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate and carboxymethylcellulose sodium, and acrylic acid polymers and copolymers, preferably formed from acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit® RS, available from Rohm & Haas, Piscatawa, N.J.) particularly preferred. Combinations of different coating materials may also be used to coat a single tablet. Preferred polymers are cellulosic polymers selected from the group consisting of hydroxypropyl cellulose, hydroxypropyl methylcellulose, methyl cellulose, ethyl cellulose, hydroxyethyl cellulose, and mixtures thereof, and a particularly preferred coating material comprises a mixture of hydroxypropyl cellulose and ethyl cellulose. The preferred weight ratio of bupropion HCl to membrane coating is in the range of approximately 6:1 to 25:1, preferably in the range of approximately 8:1 to 18:1 and most preferably about 10:1.

The pharmaceutical formulation typically will contain single unit doses of 100 mg or 150 mg of bupropion HCl and may contain single unit doses in the range of 50 mg to 200 mg.

The pharmaceutically acceptable carrier assists in stabilization and also provides for sustained release. The carrier may be a polyvinyl acetate/polyvinyl pyrrolidone mixture, a hydrogenated oil, a cellulose polymer, a carbomer or combinations and mixtures thereof. A suitable polyvinyl acetate/polyvinyl pyrrolidone mixture is Kollidon®, available from BASF, Mount Olive, N.J. Suitable hydrogenated oils include, but are not limited to, hydrogenated vegetable oil, cottonseed oil, castor oil, canola oil, palm oil, palm kernel oil and soybean oil. Suitable cellulosic polymers include, but are not limited to, hydroxypropyl cellulose, hydroxypropyl methyl cellulose, methyl cellulose and ethyl cellulose, and acrylic acid polymers and copolymers, preferably formed from acrylic acid, methacrylic acid, methyl acrylate, ethyl acrylate, methyl methacrylate and/or ethyl methacrylate, with hydroxypropyl cellulose, methyl cellulose, ethyl cellulose and Eudragit® polymers particularly preferred. Carbomers are hydroxylated vinylic polymers referred to as "interpolymers," which are prepared by crosslinking a monoolefinic acrylic acid monomer with a polyalkyl ether of sucrose. Interpolymers of this type are commercially available, e.g., under the trademark Carbopol® from the B.F. Goodrich Chemical Company. A particularly preferred polymer is a lightly crosslinked carboxypolymethylene as may be obtained commercially under the trademark Carbopol® 910.

The carrier is present in an amount effective to provide a sustained release profile such that approximately 70 wt. % to 80 wt. % of the bupropion HCl is released from the dosage form within a four-hour period and will generally make up 15 wt. % to 40 wt. % of the composition. It is important to maintain the sustained release profile as the incidence of seizures is significantly decreased when sustained release bupropion HCL formulations are administered rather than immediate release formulations. The carrier will generally be present in the range of approximately 15 wt. % to 40 wt. % of the dosage form, preferably in the range of approximately 20 wt. % to 30 wt. % and most preferably in the range of approximately 20 wt. % to 26 wt. %.

As discussed earlier, bupropion HCl is very hygroscopic and susceptible to decomposition. The inclusion of acids into bupropion HCL formulations has been used to stabilize the active agent; see U.S. Pat. Nos. 5,541,231, 5,763,493, 5,358,970, and 5,731,000 to Ruff et al. It has now been discovered that the use of large size bupropion HCl particles is also an effective method of stabilizing the drug. In a preferred embodiment of the invention, bupropion HCl crystals having a particle size in the range of approximately $75\mu$ to $900\mu$ are used to provide a stabilized formulation. Bupropion HCL particles in the range of $150\mu$ to $800\mu$ are particularly preferred and $300\mu$ particles are optimal. The large size particles may be coated or uncoated, although coated particles are preferred.

Optional components present in the dosage forms include, but are not limited to, diluents, binders, lubricants, surfactants, coloring agents, and the like. Diluents, also termed "fillers," are typically necessary to increase the bulk of a tablet so that a practical size is provided for compression. Suitable diluents include, for example, dicalcium phosphate dihydrate, calcium sulfate, lactose, cellulose, kaolin, mannitol, sodium chloride, dry starch, hydrolyzed starches, silicon dioxide, colloidal silica, titanium oxide, alumina, talc, microcrystalline cellulose, and powdered sugar. Preferred diluents herein are lactose (e.g., lactose anhydrous obtained as Pharmatose® DCL from DMV International Pharma, Veghed, Netherlands), colloidal silica (e.g., Cab-O-Sil®, obtained from Cabot Corporation, Boston Mass.), and talc. Binders are used to impart cohesive qualities to a tablet formulation, and thus ensure that a tablet remains intact after compression. Suitable binder materials include, but are not limited to, starch (including corn starch and pregelatinzed starch), gelatin, sugars (including sucrose, glucose, dextrose, lactose and sorbitol), polyethylene glycol, waxes, natural and synthetic gums, e.g., acacia, tragacanth, sodium alginate, celluloses, and Veegum, and synthetic polymers such as polymethacrylates and polyvinylpyrrolidone. Lubricants are used to facilitate tablet manufacture; examples of suitable lubricants include, for example, magnesium stearate, calcium stearate, stearic acid, glyceryl behenate, and polyethylene glycol, and are preferably present at no more than approximately 1 wt. % relative to tablet weight. A preferred lubricant herein is magnesium stearate. Surfactants may be anionic, cationic, amphoteric or nonionic surface active agents, with anionic surfactants preferred. Suitable anionic surfactants include, but are,not limited to, those containing carboxylate, sulfonate and sulfate ions, associated with cations such as sodium, potassium and ammonium ions. Particularly preferred surfactants include, but are not limited to: long alkyl chain sulfonates and alkyl aryl sulfonates such as sodium dodecylbenzene sulfonate; dialkyl sodium sulfosuccinates, such as sodium bis-(2-ethylhexyl)-sulfosuccinate; and alkyl sulfates such as sodium lauryl sulfate. If desired, the present compositions may also contain minor amounts of nontoxic auxiliary substances such as wetting or emulsifying agents, preservatives, and the like. Generally, although not necessarily, the aforementioned additives are incorporated into the body of the tablet rather than into the particle coating formulation.

It may be desirable to include one or more additional active agents in the dosage forms herein. These active agents may potentiate certain effects of bupropion hydrochloride, or vice versa. The various active agents may be present as an admixture in a tablet, or the agents may be physically segregated as in a bilayer tablet Particularly preferred additional active agents, i.e., active agents for co-administration with bupropion hydrochloride, include, but are not limited to, venlafaxine, naloxone, naltrexone, lorazepam, diazepam, chlordiazepoxide HCl, bromazepam, chlordiazepoxide, clorazepate, medazepam, oxazepam, prazepam and caffeine.

The additional active agents may be in the form of a pharmaceutically acceptable salt, ester, amide, prodrug or other derivative or analog, including active agents modified by appending one or more appropriate functionalities to enhance selected biological properties. Such modifications are known in the art and/or are described in the pertinent texts and literature.

The stabilized bupropion tablets of the invention may be manufactured using standard tablet processing procedures and equipment. Such procedures are known to those skilled in the art and described in the pertinent texts, e.g., in *Remington: The Science and Practice of Pharmacy, Nineteenth Ed.* (Easton, Pa.: Mack Publishing Company, 1995). supra. A preferred method for manufacturing the dosage form is to first coat the bupropion hydrochloride particles with the membrane coating and then form the tablet by direct compression of the coated bupropion hydrochloride and the carrier, alone or in combination with diluents, binders, lubricants, disintegrates, colorants or the like. As an alternative to direct compression, the stabilized formulation can also be prepared using a wet-granulation process. The tablet may also be molded rather than compressed; however, it is preferred that the coated bupropion hydrochloride core be manufactured using compression rather than molding. Alternatively, a drug/carrier core is prepared and a coating composition then applied using a coating pan, an airless spray technique, fluidized bed coating equipment, or the like.

The pharmaceutical compositions disclosed herein contain at least about 80% of the drug after three months when stored at about 40° C. and 75% relative humidity if the drug particles are uncoated. When the pharmaceutical composition contains coated bupropion HCl, at least about 90% remains after three months storage at about 40° C. and 75% relative humidity.

UTILITY:

The novel dosage forms are to be administered orally to a mammalian individual and, in accordance with the present invention, are used to administer bupropion hydrochloride to treat any disorder, condition or disease for which bupropion hydrochloride is generally indicated. Such disorders, conditions and diseases include, for example, depression, attention-deficit disorder (ADD), attention-deficit/hyperactivity disorder (ADHD), narcolepsy, periodic limb movement disorder, nail-biting, nicotine addiction, migraine headache, drug dependency, tardive dyskinesia, minimal brain dysfunction (MBD), high cholesterol, and psychosexual dysfunctions.

For administration of bupropion hydrochloride to treat depression, the typical daily dose is in the range of approximately 100 mg to 450 mg, preferably 200 mg to 300 mg. When used as an aid in smoking cessation, the typical daily dose is in the range of approximately 150 mg to 300 mg, preferably 300 mg. The preferred dosage regimen is 150 mg, twice daily for smoking cessation or depression. However, the exact dosage regimen will depend on a number of factors, including age, the general condition of the patient, the particular condition or disorder being treated, the severity of the patient's condition or disorder, and the like.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein, both supra and infra, are hereby incorporated by reference.

EXPERIMENTAL:

The practice of the present invention will employ, unless otherwise indicated, conventional techniques of pharmaceutical formulation, medicinal chemistry, biological testing, and the like, which are within the skill of the art. Such techniques are explained fully in the literature. Preparation of various types of pharmaceutical formulations are described, for example, in Lieberman et al. and Ansel et al., cited previously. Gibaldi and Perrier, *Pharmacokinetics* (Marcel Dekker, 1982), provide a description of the biological testing procedures useful to dosage forms such as those described and claimed herein.

In the following example, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric. All reagents were obtained commercially unless otherwise indicated.

Also, in these examples, unless otherwise stated, the abbreviations and terms employed have their generally accepted meanings. Abbreviations and tradenames are as follows (note that suppliers of each material are indicated as well):

Cab-O-Sil®=colloidal silica (Cabot Corporation, Boston Mass.);
EC=ethyl cellulose;
HPC=hydroxylpropyl cellulose;
Kollidon® SR=polyvinyl acetate/polyvinyl pyrrolidone (BASF, Mount Olive, N.J.);
Methocel® A4M=methylcellulose (Dow Chemical, Midland, Mich.);
Pharmatose® DCL 21=lactose (DMV International Pharma, Veghed, Netherlands); and
Sterotex® HM=hydrogenated soybean oil (Abitec Corporation, Columbus, Ohio.).

All patents, patent applications, journal articles and other references mentioned herein are incorporated by reference in their entireties.

EXAMPLES 1–4

BUPROPION HCL 100 mg FORMULATIONS

The following bupropion HCL formulations were prepared by blending the ingredients and compressing them to form a tablet.

TABLE 1

100 mg Bupropion HCl Formulations

| Ingredient | Example Number/Weight (mg) per Tablet | | | |
|---|---|---|---|---|
|  | 1 | 2 | 3 | 4 |
| Bupropion HCl (coated with HPC & EC)* | 110.00 | 110.00 | 110.00 | — |
| Bupropion HCl (uncoated) | — | — | — | 100.00 |
| HPC | 70.00 | — | — | — |
| Methocel ® A4M | 15.00 | — | — | — |
| Pharmatose ® DCL 21 | 121.30 | 121.30 | 116.10 | 121.30 |
| Talc | 27.00 | 27.00 | 25.00 | 27.00 |
| Magnesium Stearate | 0.70 | 0.70 | 0.70 | 0.70 |
| Kollidon ® SR | — | 85.00 | — | 85.00 |
| Sterotex ® HM | — | — | 70.00 | — |
| Cab-O-Sil ® | — | — | 0.20 | — |
| Total Weight | 344.00 | 344.00 | 322.00 | 334.00 |

*Coating is 5% wt. HPC, 5% wt. EC.

EXAMPLE 5

DISSOLUTION PROFILES OF BUPROPION HCl 100 mg FORMULATIONS

The bupropion HCl formulations detailed in Examples 1–4 and a 100 mg Wellbutrin® SR tablet were each placed in 900 ml of water and stirred with a paddle at 50 rpm. The dissolution profiles of each formulation are presented in Table 2.

TABLE 2

Formulation Dissolution Profiles

| Time | Sample/Percent Bupropion HCl Dissolved | | | |
|---|---|---|---|---|
|  | 1 | 2 | 3 | 4 |
| 0.5 hour | 18 | 24 | 36 | 48 |
| 1 hour | 32 | 39 | 48 | 69 |
| 2 hour | 54 | 55 | 67 | 99 |
| 3 hour | 68 | 67 | 79 | 101 |
| 4 hour | 78 | 76 | 87 | 101 |
| 6 hour | 91 | 87 | 97 | 101 |
| 8 hour | 94 | 91 | 99 | 101 |

* Lot No. 646241

EXAMPLE 6

STABILITY OF BUPROPION HCl 100 mg FORMULATIONS

The bupropion HCl formulations of Examples 1–4 were coated with a solvent seal coat and a solvent/water color coat. The seal coat, hydroxypropyl cellulose, resulted in a 2% (w/w) weight gain and the color coat, Opadry Blue YS-1-10699, resulted in a 3%(w/w) weight gain. The assay percentage results of the stability samples are presented in Table 3.

TABLE 3

Stability of 100 mg Bupropion HCl Formulations

| Duration and Conditions | Example Number/(%) Bupropion HCl Present | | | |
|---|---|---|---|---|
|  | 1 | 2 | 3 | 4 |
| Coated Tablet (Packaged in HDPE Bottles with Induction Sealing) | | | | |
| 1 month at 40° C./75% RH | 98.8% | 97.6% | 99.3% | 95.7% |
| 2 months at 40° C./75% RH | 94.7% | 93.6% | 96.0% | 97.6% |
| 3 months at 40° C./75% RH | 93.6% | 91.8% | 96.1% | 95.4% |

* RT = Room Temperature
** RH = Relative Humidity

What is claimed is:

1. A pharmaceutical composition for oral administration, comprising a solid dosage form that is free of added acid and contains a therapeutically effective amount of particulate, crystalline bupropion hydrochloride as an active agent and a pharmaceutically acceptable carrier that provides for sustained release of the active agent from the dosage form, wherein the composition contains at least about 80 wt. % of undegraded bupropion hydrochloride after storage for three months at about 40° C. and 75% relative humidity.

2. The composition of claim 1, wherein the dosage form comprises a compressed tablet.

3. The composition of claim 1, wherein the bupropion hydrochloride has a particle size in the range of approximately 75μ to 900μ.

4. The composition of claim 3, wherein the bupropion hydrochloride has a particle size in the range of approximately 150μ to 800μ.

5. The composition of claim 1, wherein the bupropion hydrochloride is coated with a membrane coating material.

6. The composition of claim 5, wherein the membrane coating material is effective to provide a sustained release profile wherein approximately 70 wt. % to 80 wt. % of the bupropion hydrochloride is released from the dosage form within a four-hour period.

7. The composition of claim 6, wherein the membrane coating material comprises a cellulosic polymer.

8. The composition of claim 7, wherein the cellulosic polymer is selected from the group consisting of hydroxypropyl cellulose, hydroxypropyl methylcellulose, methyl cellulose, ethyl cellulose, hydroxyethyl cellulose, and mixtures thereof.

9. The composition of claim 8, wherein the membrane coating material comprises a mixture of hydroxypropyl cellulose and ethyl cellulose.

10. The composition of claim 3, wherein the weight ratio of bupropion hydrochloride to membrane coating material is in the range of approximately 6:1 to 25:1.

11. The composition of claim 10, wherein the weight ratio of bupropion hydrochloride to membrane coating material is in the range of approximately 8:1 to 18:1.

12. The composition of claim 11, wherein the weight ratio of bupropion hydrochloride to membrane coating material is approximately 10:1.

13. The composition of claim 1, wherein the carrier represents in the range of approximately 15 wt. % to 40 wt. % of the dosage form.

14. The composition of claim 1, wherein the carrier is selected from the group consisting of (a) a mixture of polyvinyl acetate and polyvinyl pyrrolidone, (b) a hydrogenated oil, (c) a carbomer, (d) hydroxypropyl cellulose, (e) methyl cellulose, (f) ethyl cellulose, (g) acrylic acid polymers and copolymers, or a combination thereof.

15. The composition of claim 14, wherein the carrier comprises a mixture of polyvinyl acetate and polyvinyl pyrrolidone.

16. The composition of claim 15, wherein the carrier comprises a mixture of approximately 80 wt. % polyvinyl acetate, 19 wt. % polyvinyl pyrrolidone, 0.8 wt. % sodium lauryl sulfate and 0.2% colloidal silica.

17. The composition of claim 14, wherein the carrier comprises a hydrogenated oil.

18. The composition of claim 17, wherein the hydrogenated oil is selected from the group consisting of hydrogenated vegetable oil, cottonseed oil, castor oil, canola oil, palm oil, palm kernel oil, soybean oil, and mixtures thereof.

19. A pharmaceutical composition for oral administration, comprising a solid dosage form that is free of added acid and contains a therapeutically effective amount of particulate, crystalline bupropion hydrochloride as an active agent and a pharmaceutically acceptable carrier that provides for sustained release of the active agent from the dosage form, wherein the composition contains at least about 80 wt. % of undegraded bupropion hydrochloride after storage for three months at about 40° C. and 75% relative humidity and the carrier is comprised of hydrogenated soybean oil.

20. A pharmaceutical composition for oral administration, comprising a solid dosage form that is free of added acid and contains a therapeutically effective amount of particulate, crystalline bupropion hydrochloride as an active agent and a pharmaceutically acceptable carrier that provides for sustained release of the active agent from the dosage form, wherein the composition contains at least about 80 wt. % of undegraded bupropion hydrochloride after storage for three months at about 40° C. and 75% relative humidity and the carrier is comprised of a carbomer.

21. The composition of claim 1, wherein the therapeutically effective amount of bupropion hydrochloride is a unit dosage.

22. The composition of claim 21, wherein the therapeutically effective amount is approximately 100 mg.

23. The composition of claim 21, wherein the therapeutically effective amount is approximately 150 mg.

24. A sustained release bupropion hydrochloride composition, comprising a compressed tablet that is free of added acid and contains:

approximately 100 mg to 150 mg bupropion hydrochloride crystals having a particle size in the range of approximately 150$\mu$ to 800$\mu$, said crystals coated with a cellulosic polymer selected from the group consisting of hydroxypropyl cellulose, hydroxypropyl methylcellulose, methyl cellulose, ethyl cellulose, hydroxyethyl cellulose and mixtures thereof, wherein the weight ratio of bupropion hydrochloride to cellulosic polymer is in the range of approximately 8:1 to 18:1; and a pharmaceutically acceptable carrier effective to provide sustained release of the bupropion hydrochloride such that approximately 70% to 90% of the bupropion hydrochloride is released from the tablet within four hours of oral administration, wherein the carrier is selected from the group consisting of (a) a mixture of polyvinyl acetate and polyvinyl pyrrolidone, (b) a hydrogenated oil, (c) a carbomer, (d) hydroxypropyl cellulose, (e) methyl cellulose, (f) ethyl cellulose, (g) acrylic acid polymers and copolymers, and mixtures thereof, wherein the composition contains at least about 90 wt. % of undegraded bupropion hydrochloride after storage for three months at about 40° C. and 75% relative humidity.

25. A method for preparing a stabilized bupropion hydrochloride composition for oral administration without addition of acid, comprising admixing particulate, crystalline bupropion hydrochloride with a pharmaceutically acceptable carrier selected from the group consisting of (a) a mixture of polyvinyl acetate and polyvinyl pyrrolidone, (b) a hydrogenated oil, (c) a carbomer, (d) hydroxypropyl cellulose, (e) methyl cellulose, (f) ethyl cellulose, (g) acrylic acid polymers and copolymers, and mixtures thereof, and compressing the admixture so formed into a tablet, wherein the composition contains at least about 80 wt. % of undegraded bupropion hydrochloride after storage for three months at about 40° C. and 75% relative humidity.

26. The method of claim 25, wherein the bupropion hydrochloride has a particle size in the range of approximately 75$\mu$ to 900$\mu$.

27. The composition of claim 26, wherein the bupropion hydrochloride has a particle size in the range of approximately 150$\mu$ to 800$\mu$.

28. A method for preparing a stabilized bupropion hydrochloride composition for oral administration without addition of acid, comprising:

(a) coating particulate, crystalline bupropion hydrochloride with an amount of a cellulosic polymer effective to provide a weight ratio of bupropion hydrochloride to cellulosic polymer in the range of approximately 8:1 to 18:1, and wherein the cellulosic polymer is selected from the group consisting of hydroxypropyl cellulose, hydroxypropyl methylcellulose, methyl cellulose, ethyl cellulose, hydroxyethyl cellulose and mixtures thereof;

(b) admixing the coated bupropion hydrochloride with a pharmaceutically acceptable carrier selected from the group consisting of a mixture of polyvinyl acetate and polyvinyl pyrrolidone, a hydrogenated oil, a carbomer, hydroxypropyl cellulose, methylcellulose, ethylcellulose, acrylic acid polymers and copolymers, and mixtures thereof; and (c) compressing the admixture so formed into a tablet, wherein the composition contains at least about 80 wt. % of undegraded bupropion hydrochloride after storage for three months at about 40° C. and 75% relative humidity.

29. The method of claim 28, wherein the bupropion hydrochloride has a particle size in the range of approximately 75$\mu$ to 900$\mu$.

30. The composition of claim 29, wherein the bupropion hydrochloride has a particle size in the range of approximately 150$\mu$ to 800$\mu$.

31. A method for treating depression in a patient in need of such treatment, comprising orally administering to the patient the pharmaceutical composition of claim 1.

32. A method for treating depression in a patient in need of such treatment, comprising orally administering to the patient the pharmaceutical composition of claim 24.

33. A method for treating nicotine dependency in a patient in need of such treatment, comprising orally administering to the patient the pharmaceutical composition of claim 1.

34. A method for treating nicotine dependency in a patient in need of such treatment, comprising orally administering to the patient the pharmaceutical composition of claim 24.

35. The method of claim 33, wherein the treatment additionally comprises administering an effective amount of nicotine.

36. The method of claim 34, wherein the treatment additionally comprises administering an effective amount of nicotine.

* * * * *